US012642490B2

(12) United States Patent
Li et al.

(10) Patent No.: US 12,642,490 B2
(45) Date of Patent: Jun. 2, 2026

(54) DETECTING SYSTEM AND DIAGNOSTIC METHOD USING THE SAME

(71) Applicant: INDUSTRIAL TECHNOLOGY RESEARCH INSTITUTE, Hsinchu (TW)

(72) Inventors: Yun-Huan Li, Kaohsiung City (TW); Uma Sankar Rout, Balasore (IN)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 364 days.

(21) Appl. No.: 18/083,987

(22) Filed: Dec. 19, 2022

(65) Prior Publication Data

US 2024/0197259 A1 Jun. 20, 2024

(51) Int. Cl.
*A61B 5/00* (2006.01)

(52) U.S. Cl.
CPC . *A61B 5/72* (2013.01); *A61B 5/68* (2013.01)

(58) Field of Classification Search
None
See application file for complete search history.

(56) References Cited

U.S. PATENT DOCUMENTS

| | | | |
|---|---|---|---|
| 5,508,602 A | 4/1996 | Borgato et al. | |
| 7,556,135 B2 | 7/2009 | Kasuya | |
| 10,067,175 B2 | 9/2018 | Ramirez et al. | |
| 10,241,143 B2 | 3/2019 | Park et al. | |

| | | | |
|---|---|---|---|
| 11,249,129 B2 | 2/2022 | Zhang et al. | |
| 2004/0008016 A1* | 1/2004 | Sutardja | H02M 3/157 |
| | | | 323/283 |
| 2006/0195254 A1 | 8/2006 | Ladetto et al. | |
| 2007/0115954 A1* | 5/2007 | Wu | G06F 13/4072 |
| | | | 370/359 |
| 2008/0079511 A1* | 4/2008 | Chou | H03H 7/40 |
| | | | 333/17.3 |
| 2012/0032684 A1 | 2/2012 | Siddiquie et al. | |

(Continued)

FOREIGN PATENT DOCUMENTS

| | | |
|---|---|---|
| CN | 104008157 A | 8/2014 |
| CN | 206223807 U | 6/2017 |

(Continued)

OTHER PUBLICATIONS

Chiu Chih-Chung et al. ; Intelligent diagnosis system for power module and method thereof; Publication: Jun. 1, 2018; TW201819938A; Ind Tech Res Inst [TW]; (Year: 2018).*

(Continued)

*Primary Examiner* — Nasima Monsur
(74) *Attorney, Agent, or Firm* — Birch, Stewart, Kolasch & Birch, LLP

(57) ABSTRACT

A detecting system and a diagnostic method applying the same are provided. The detecting system comprises a power module, a sensing module and a processing module. The sensing module electrically connected to the power module. The sensing module is configured to measure the impedance value of at least one signal terminal of the power module. The processing module electrically connected to the sensing module. The processing module is configured to receive the impedance value and determine whether the impedance value meets an abnormal threshold.

12 Claims, 3 Drawing Sheets

(56) References Cited

U.S. PATENT DOCUMENTS

| | | | | |
|---|---|---|---|---|
| 2015/0285867 | A1 * | 10/2015 | Wang ................... | G01R 31/367 |
| | | | | 702/63 |
| 2017/0179830 | A1 * | 6/2017 | Tang ..................... | H02M 3/158 |
| 2019/0044429 | A1 * | 2/2019 | Yang ................... | H02M 7/5395 |

FOREIGN PATENT DOCUMENTS

| | | | |
|---|---|---|---|
| CN | 108370218 | B | 2/2021 |
| CN | 112964973 | A | 6/2021 |
| CN | 114024343 | A | 2/2022 |
| JP | 2020-169984 | A | 10/2020 |
| TW | I321623 | B | 3/2010 |
| TW | 201526519 | A | 7/2015 |
| TW | 201819938 | A | 6/2018 |
| TW | 201819941 | A | 6/2018 |

OTHER PUBLICATIONS

Baker et al.,"Simultaneous On-State Voltage and Bond-Wire Resistance Monitoring of Silicon Carbide MOSFETs" Energies 2017, vol. 10, No. 384, Jan. 12, 2017 (published on Mar. 18, 2017), pp. 1-8.

Ciappa,"Selected Failure Mechanisms of Modern Power Modules" Microelectronics Reliability, vol. 42, Jan. 31, 2002, pp. 653-667.

Dornic et al.,"Analysis of the Degradation Mechanisms Occurring in the Topside Interconnections of IGBT Power Devices During Power Cycling" Microelectronics Reliability, vol. 88-90, Sep. 30, 2018, pp. 462-469.

Ibrahim et al.,"Using of Bond-Wire Resistance as Aging Indicator of Semiconductor Power Modules" Microelectronics Reliability, vol. 114, Nov. 1, 2020, pp. 1-7.

Luo et al.,"A Study on the Effect of Bond Wires Lift-Off on IGBT Thermal Resistance Measurement" Electronics 2021, vol. 10, No. 194, Jan. 15, 2021, pp. 1-15.

Martineau et al.,"Universal Mechanisms of Al Metallization Ageing in Power MOSFET Devices" Microelectronics Reliability, vol. 54, Jul. 15, 2014, pp. 2432-2439.

Taiwanese Office Action and Search Report for Taiwanese Application No. 112100088, dated Dec. 19, 2023.

* cited by examiner

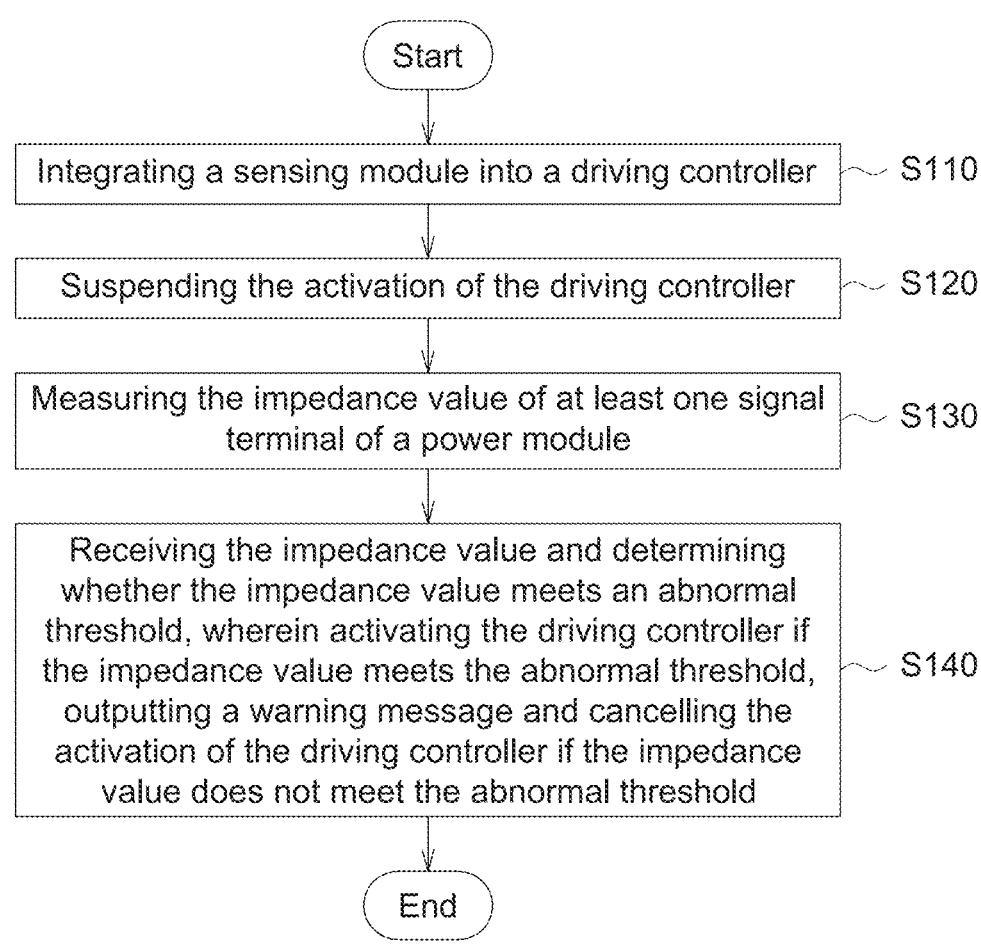

S

Start

Integrating a sensing module into a driving controller — S110

Suspending the activation of the driving controller — S120

Measuring the impedance value of at least one signal terminal of a power module — S130

Receiving the impedance value and determining whether the impedance value meets an abnormal threshold, wherein activating the driving controller if the impedance value meets the abnormal threshold, outputting a warning message and cancelling the activation of the driving controller if the impedance value does not meet the abnormal threshold — S140

End

FIG. 4

DETECTING SYSTEM AND DIAGNOSTIC METHOD USING THE SAME

TECHNICAL FIELD

The disclosure relates to a detecting system and a diagnostic method applying the same, particularly relates to a detecting system and a diagnostic method for motor driving controllers.

BACKGROUND

In prior art of a power module of a motor driving controller, the signal terminals of the power module have problems like the poor contact due to factors such as production defects, driving vibration and long-term use, causing a reduced performance of an electric vehicle or a sudden loss of power when driving. Therefore, those skilled in the art strive to solve the above-mentioned problems.

SUMMARY

According to an aspect of the present disclosure, a detecting system is provided. The detecting system comprises a power module, a sensing module and a processing module. The sensing module electrically connected to the power module. The sensing module is configured to measure the impedance value of at least one signal terminal of the power module. The processing module electrically connected to the sensing module. The processing module is configured to receive the impedance value and determine whether the impedance value meets an abnormal threshold.

According to another aspect of the present disclosure, a diagnostic method, which applies the detecting system of the present disclosure, is provided. The diagnostic method comprises: integrating the sensing module into a driving controller; suspending the activation of the driving controller; measuring the impedance value of the at least one signal terminal of the power module; receiving the impedance value and determining whether the impedance value meets the abnormal threshold, wherein activating the driving controller if the impedance value meets the abnormal threshold, outputting a warning message and cancelling the activation of the driving controller if the impedance value does not meet the abnormal threshold.

The disclosure will become apparent from the following detailed description of the preferred but non-limiting embodiments. The following description is made with reference to the accompanying drawings.

BRIEF DESCRIPTION OF THE DRAWINGS

FIG. 4 shows a flow chart of the diagnostic method applying the detecting system according to an embodiment of the present disclosure.

DETAILED DESCRIPTION

Figure 1:
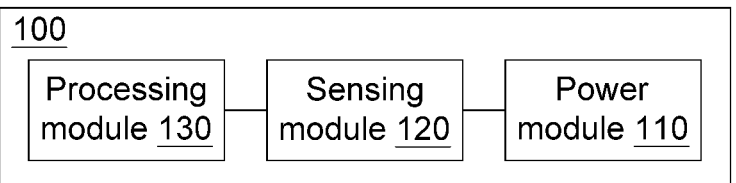
FIG. 1 shows a schematic block diagram of the detecting system according to an embodiment of the present disclosure.

The embodiments of the present disclosure will be described in detail below, together with the drawings as examples. In addition to these detailed descriptions, the present disclosure may also be widely implemented in other embodiments, and any simple replacement, modification and equivalent change of the described embodiment(s) are included in the scope of the present disclosure.

In the following detailed description, for purpose of explanation, numerous details are set forth in order to provide a thorough understanding of the disclosed embodiments. However, the disclosure may be practiced under omitting some or all of these details. Also, well-known steps and elements are not described in detail in order to avoid unnecessarily limitation to the present disclosure. The same or similar elements in the drawings have the same or similar reference signs. It should be noted that the drawings are for illustrative purpose only and do not mean the actual size or quantity of elements, unless otherwise described.

Figure 2:
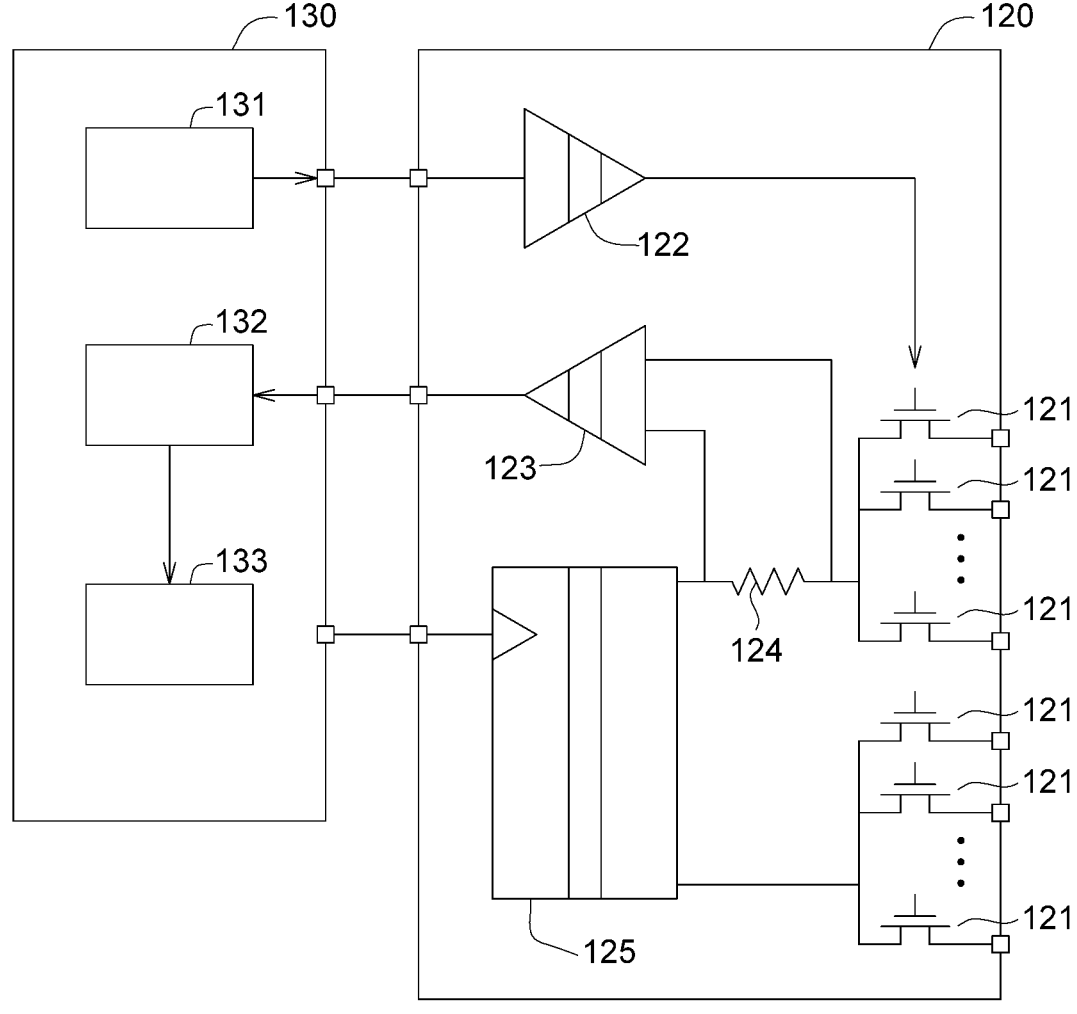
FIG. 2 shows a schematic configuration diagram of a sensing module and a processing device of the detecting system according to an embodiment of the present disclosure.
Figure 3:
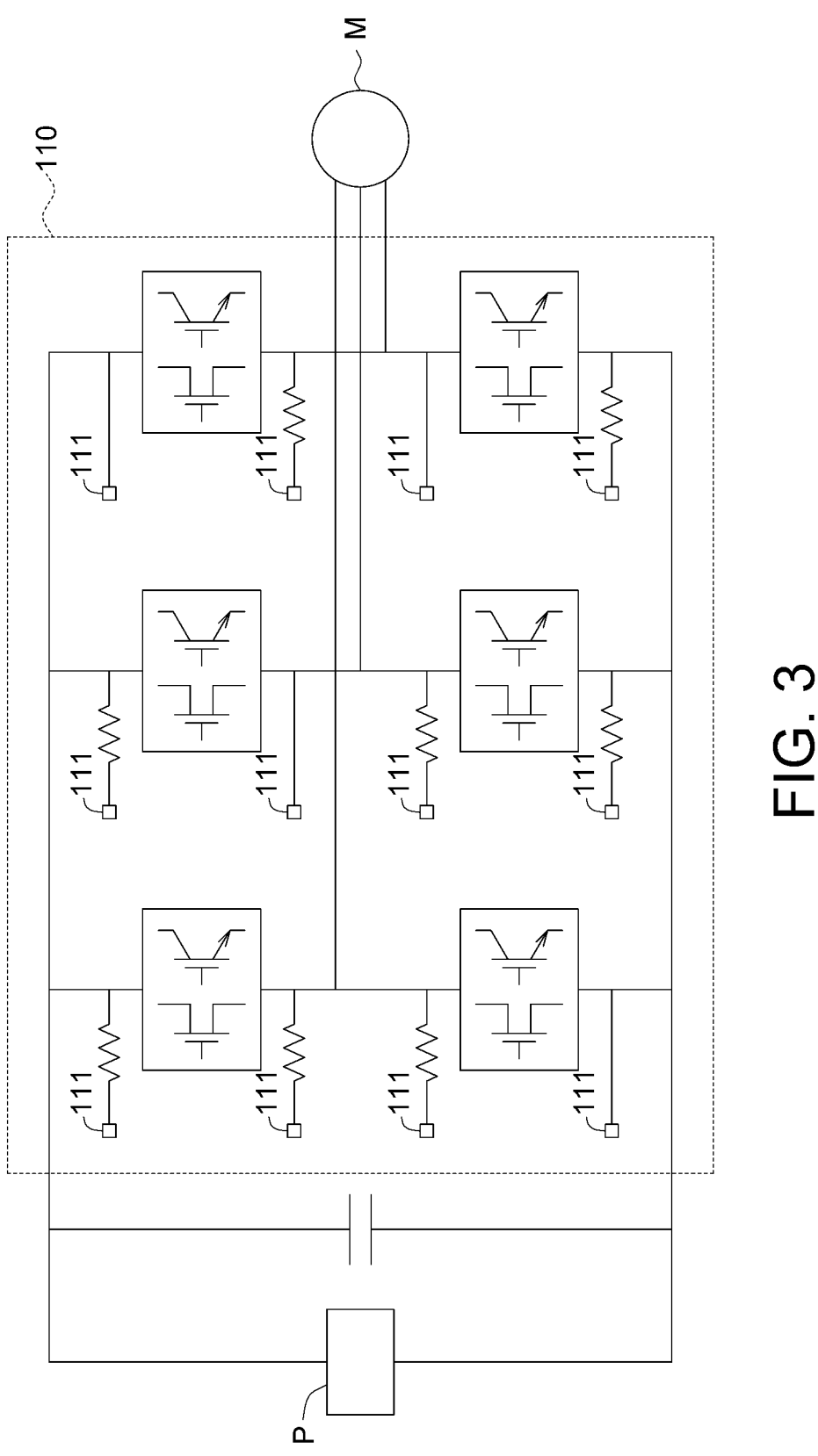
FIG. 3 shows a schematic configuration diagram of a power module of the detecting system according to an embodiment of the present disclosure.

Please refer to FIG. 1 to FIG. 3, FIG. 1 shows a schematic block diagram of a detecting system 100 according to an embodiment of the present disclosure, FIG. 2 shows a schematic configuration diagram of a sensing module 120 and a processing module 130 of the detecting system 100 of the present disclosure, and FIG. 3 shows a schematic configuration diagram of a power module 110 of the detecting system 100 of the present disclosure.

The detecting system 100 mainly comprises a power module 110, a sensing module 120 and a processing module 130. The power module 110 may be, for example, a power module used for motor control in the field of electric vehicles. The sensing module 120 may be, for example, a sensing circuit that is able to be electrically connected to the power module 110. The sensing module 120 is configured to measure the impedance value of at least one signal terminal 111 of the power module 110. For example, the sensing module 120 measures the resistance value at the signal terminal 111 of the power module 110.

The processing module 130 may be, for example, a processor that is able to be electrically connected to the sensing module 120. The processing module 130 is configured to receive the measured impedance value and determine whether the impedance value meets an abnormal threshold. In 20) detail, the abnormal threshold means that the processing module 130 determines whether the impedance value (such as a resistance value) of the signal terminal 111 is higher than a preset threshold resistance value, so as to determine whether there is an abnormal situation. For example, the preset threshold resistance value may be set to a micro-ohm level, so that the resistance value corresponding to an abnormal situation is generally an ohm level.

The power module 110 may include a plurality of signal terminals 111. The sensing module 120 may include a plurality of switch elements 121. The switch elements 121 may be electrically connected to the signal terminals 111 respectively, so as to achieve the measurement of multiple sets of signal terminals 111. Take FIG. 3 of the present disclosure as an example, the power module 110 is a configuration of a so-called three-phase six-pulse bridge. The power module 110 may be connected to a power supply P, such as a DC power supply. The power module 110 may be further connected to a motor M to serve as a power module of the motor.

In addition, the sensing module 120 may include a buffer 122. The buffer 122 may be electrically connected to the switch elements 121. The processing module 130 may include a selector 131. The buffer 122 may be electrically connected between the selector 131 and the switch elements 121, so that the processing module 130 is able to selectively switch the switch elements 121, thereby performing the measurement on different sets of signal terminals 111 in sequence.

Further, the sensing module 120 may further include a buffer 123. The processing module 130 may include a comparator 132. The buffer 123 is electrically connected to the comparator 132. The sensing module 120 may receive the impedance value measured by the sensing module 120 through the comparator 132. The comparator 132 is configured to compare the impedance value with a preset threshold value to determine whether the impedance value meets the abnormal threshold.

As mentioned above, the impedance value measured by the sensing module 120 may be, for example, a resistance value, and the preset threshold value may be, for example, a preset threshold resistance value. The comparator 132 may compare this resistance value with the preset threshold resistance value to determine whether the resistance value is higher than the preset threshold resistance value, so as to determine whether there is an abnormal situation. Moreover, the processing module 130 may include a register 133. The register 133 is electrically connected to the comparator 132. The register 133 is configured to temporarily store the determination result of whether the impedance value obtained by the comparator 132 meets the abnormal threshold, in order to prepare for subsequent use.

The sensing module 120 may include an impedance element 124 and a regulator 125. The impedance element 124 may be, for example, a resistor that is able to be electrically connected to the buffer 123 and the signal terminals 111 of the power module 110, and the regulator 125 may be electrically connected to the impedance element 124 and the power module 120. The processing module 130 may be configured to perform a voltage division calculation according to the impedance value of the impedance element 124, so as to obtain the impedance values at the signal terminals 111 of the power module 110. In detail, the processing module 130 may perform a voltage division calculation of impedance based on an equivalent circuit formed by the impedance element 124, the regulator 125 and a set of signal terminal 111 to obtain the impedance value at the set of signal terminal 111 of the power module 110.

Please refer to FIG. 4, FIG. 4 shows a flow chart of the diagnostic method S applying the detecting system according to an embodiment of the present disclosure. In this embodiment, the following diagnostic method S is performed with the detecting system 100 shown in FIG. 1. The steps S110 to S140 of the diagnostic method S are described as follows.

In the step S110, integrate the sensing module 120 into a driving controller, such as a motor driving controller that includes the power module 110. In the step S120, suspend the activation of the driving controller. That is, a driving circuit of the motor driving controller is turned off. In the step S130, measure the impedance value of at least one signal terminal 111 of the power module 110 through the integrated sensing module 120. In the step S140, receive the measured impedance value through the processing module 130 and determine whether the impedance value meets the aforementioned abnormal threshold.

In the step S140, if the impedance value does not meet the abnormal threshold, then activate the driving controller. Or, if the impedance value meets the abnormal threshold, then output a warning message and cancel the activation of the driving controller. In detail, the warning information may be provided to users via a user interface. In one embodiment, if the impedance value meets the abnormal threshold, the driving controller is able to be directed to enter an abnormal mode, such as a low power mode. As such, the diagnostic method S of the embodiment of the present disclosure is able to determine whether the motor driving controller has an abnormal situation by measuring the impedance of the power module of the motor driving controller before the original diagnostic procedure of an electric vehicle where the motor driving controller is installed, thereby providing a warning message to users.

According to the detecting system and the diagnostic method using the same described above, the sensing module is able to measure the impedance value at the signal terminal of the power module, and the processing module is able to receive the impedance value and determine whether the impedance value meets an abnormal threshold to know the reliability of the signal terminal of the power module, and then provide a warning message to users.

While the disclosure has been described and illustrated with reference to specific embodiments thereof, these descriptions and illustrations do not limit the disclosure. It should be understood by those skilled in the art that various changes may be made and equivalents may be substituted without departing from the true spirit and scope of the disclosure as defined by the appended claims. The illustrations may not necessarily be drawn to scale. There may be distinctions between the artistic renditions in the present disclosure and the actual apparatus due to manufacturing processes and tolerances. There may be other embodiments of the present disclosure which are not specifically illustrated. The specification and the drawings are to be regarded as illustrative rather than restrictive. Modifications may be made to adapt a particular situation, material, composition of matter, method, or process to the objective, spirit and scope of the disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not limitations of the disclosure.

What is claimed is:

1. A detecting system, comprising:
   a power module being a configuration of a three-phase six-pulse bridge and including a plurality of signal terminals;
   a sensing circuit electrically connected to the power module and configured to actively measure an impedance value of the plurality of signal terminals of the power module, wherein the sensing circuit includes a plurality of switch elements respectively electrically connected to the plurality of signal terminals to select one of the signal terminals for measurement; and
   a processing module electrically connected to the sensing circuit, wherein the processing module is configured to receive the impedance value and determine whether the impedance value meets an abnormal threshold,
   wherein the processing module includes a comparator, the comparator is configured to compare the impedance value with a preset threshold value to determine whether the impedance value meets the abnormal threshold value,
   wherein the sensing circuit includes an impedance element and a regulator, the impedance element is electrically connected to the plurality of signal terminals, the regulator is electrically connected to the impedance element and the power module, and the processing module is configured to perform a voltage division calculation of impedance based on an equivalent circuit formed by the impedance element, the regulator and one of the plurality of signal terminals to obtain the impedance value at the one of the plurality of signal terminals.

2. The detecting system according to claim 1, wherein the sensing circuit includes a buffer electrically connected to the switch elements.

3. The detecting system according to claim 2, wherein the processing module includes a selector, the buffer is electrically connected between the selector and the switch elements, and the selector is configured to selectively switch the switch elements.

4. The detecting system according to claim 1, wherein the sensing circuit includes a buffer electrically connected to the comparator.

5. The detecting system according to claim 4, wherein the impedance element is electrically connected to the buffer.

6. The detecting system according to claim 1, wherein the processing module includes a register, the register is electrically connected to the comparator, and the register is configured to temporarily store a determination result of whether the impedance value meets the abnormal threshold.

7. A diagnostic method applying the detecting system according to claim 1, comprising:

integrating the sensing circuit into a driving controller;

suspending the activation of the driving controller;

measuring the impedance value of the plurality of signal terminals of the power module, and receiving the impedance value and determining whether the impedance value meets the abnormal threshold, wherein activating the driving controller if the impedance value meets the abnormal threshold, outputting a warning message and cancelling the activation of the driving controller if the impedance value does not meet the abnormal threshold.

8. The diagnostic method according to claim 7, wherein the sensing circuit includes a buffer electrically connected to the switch elements.

9. The diagnostic method according to claim 8, wherein the processing module includes a selector, the buffer is electrically connected between the selector and the switch elements, and the selector is configured to selectively switch the switch elements.

10. The diagnostic method according to claim 7, wherein the sensing circuit includes a buffer electrically connected to the comparator.

11. The diagnostic method according to claim 10, wherein the impedance element is electrically connected to the buffer.

12. The diagnostic method according to claim 7, wherein the processing module includes a register, the register is electrically connected to the comparator, and the register is configured to temporarily store a determination result of whether the impedance value meets the abnormal threshold.

* * * * *